United States Patent [19]

von Magius

[11] Patent Number: 4,952,590
[45] Date of Patent: Aug. 28, 1990

[54] ETHOXYQUIN SALTS OF ALKANOIC ACIDS AND USE THEREOF FOR PRESERVING FISH AND GRASS MEALS

[76] Inventor: Niels W. von Magius, Långövägen 7, Helsingborg S-253 72, Sweden

[21] Appl. No.: 230,888

[22] Filed: Aug. 11, 1988

Related U.S. Application Data

[63] Continuation of Ser. No. 919,620, Oct. 15, 1986, Pat. No. 4,772,710, which is a continuation of Ser. No. 713,394, filed as PCT DK84/00067 on Jul. 12, 1984 published as WO85/00601 on Feb. 14, 1985, abandoned.

[51] Int. Cl.$^5$ ............... C07D 215/20; A23K 3/00
[52] U.S. Cl. ................................. 514/311; 546/178
[58] Field of Search .............. 546/178; 514/311; 99/8

[56] References Cited

U.S. PATENT DOCUMENTS

| | | | |
|---|---|---|---|
| 2,562,970 | 8/1951 | Thompson | 546/178 |
| 2,661,277 | 12/1953 | Mowry et al. | 546/178 |

*Primary Examiner*—David B. Springer
*Attorney, Agent, or Firm*—Birch, Stewart, Kolasch & Birch

[57] ABSTRACT

Salts of ethoxyquin with an alkanoic acid containing 1-5 carbon atoms and with citric acid are provided. Such salts exhibit superior properties compared to ethoxyquin regarding viscosity, solubility in water and/or increasing viscosity due to polymerization, and are useful for i.a. oxidation-protection of bulk materials such as fishmeal, and as agents against fruit scab.

10 Claims, No Drawings

ETHOXYQUIN SALTS OF ALKANOIC ACIDS AND USE THEREOF FOR PRESERVING FISH AND GRASS MEALS

This application is a continuation of copending application Ser. No. 06/919,620, filed on Oct. 15, 1986 which in turn is a continuation of application Ser. No. 713,394 filed as PCT DK84/00067 on Jul. 12, 1984, published as WO85/00601 on Feb. 14, 1985, now abandoned.

The present invention relates to novel salts of ethoxyquin.

DESCRIPTION OF THE PRIOR ART

Ethoxyquin (6-ethoxy-1,2-dihydro-2,2,4-trimethylquinoline) is used extensively as an antioxidant, particularly for bulk materials such as fishmeal or grass in order on the one hand to avoid oxidation degradation such as rancidity and on the other hand to avoid explosions. Normally, ethoxyquin is applied in concentrations in the range of 100-500 ppm.

Ethoxyquin itself, however, suffers from several drawbacks. Firstly, pure ethoxyquin is a viscous oil at normal temperatures (about 2,000 cps at 20° C.) and the viscosity increases rapidly with decreasing temperature (approximately 6000-7000 cps at 10° C.) Also, the viscosity of technical grades of ethoxyquin, which may contain anywhere from 90% ethoxyquin down to 50-60% or even less, increases substantially with increasing content of impurities, and at the same time, a given ethoxyquin product will also increase in viscosity when not protected by an inert atmosphere such as $N_2$. The increase in viscosity is caused by a polymerization reaction which in turn is caused by the presence of oxygen and accelerated by the influence of light. The high viscosity makes it very difficult to evenly distribute ethoxyquin into bulk materials such as fishmeal in such low amounts as the above-mentioned 100-500 ppm. There will be a tendency towards the occurrence of localized high concentrations of ethoxyquin in the bulk material leading to bad oxidation-protection in other parts of the material. Secondly, ethoxyquin is only soluble in water in very low concentrations, which makes it impracticable to attempt to distribute ethoxyquin into a bulk product as an aqueous solution.

In order to overcome the above-mentioned problems, it has previously been attempted to use ethoxyquin absorbed into silica gel or as an emulsifier-stabilized suspension (stabilized with Tween ® 80 or other emulsifiers) in order to obtain a more readily distributable form of ethoxyquin.

Even such forms, however, suffer from the drawbacks concerning the keeping qualities of ethoxyquin in general. As mentioned above, both oxygen and the influence of light tend to degrade ethoxyquin.

In a further attempt to overcome the problems connected with ethoxyquin, some salts have been prepared in the prior art, viz. the hydrochloride, the sulphate, the phosphate and the succinate. Unfortunately, such salts, which themselves are crystalline, are not very soluble in water, the solubility of e.g. the hydrochloride being only approximately 5% by weight.

Ethoxyquin also finds use as a protection agent against apple scab, where the apples are dipped into an emulsifier-stabilized solution of ethoxyquin in water, the concentration of ethoxyquin being in the order of 2 ppm. The preparation of such a dipping mixture is somewhat complicated and involves mixing a mixture of ethoxyquin and emulsifier (e.g. Tween ® 80) into a solution of the same emulsifier in water.

SUMMARY OF THE INVENTION

The present invention obviates or substantially reduces the above-discussed disadvantages of the ethoxyquin forms according to the prior art both as regards viscosity, solubility in water and/or increasing viscosity due to oxidation-caused polymerization.

The invention relates to a salt ethoxyquin with an alkanoic acid containing 1-5 carbon atoms.

DETAILED DESCRIPTION OF THE INVENTION

As examples of alkanoic acids with 1-5 carbon atoms may be mentioned formic acid, acetic acid, propionic acid, butyric acid, isobutyric acid, and valeric acid. Among these acids, formic acid is preferred.

Salts of the above-described kind are characterized by solubility in or miscibility with water and/or in that they are liquids themselves. For example, ethoxyquin formiate is soluble in water and is itself a liquid even at $-18°$ C.

It also appears that the salts of the invention, which are liquid, do not to any significant extent undergo increase in viscosity when subjected to the influence of oxygen and light. It is assumed that this is due to the fact that the formulation of ethoxyquin ions inhibits the rearrangement and radical reactions that form a part of the polymerization process. Salts of the above-described type exhibit a longer shelf life than ethoxyquin when subjected to oxygen and light.

Furthermore, even if the viscosity of such salts should be too high for certain applications, the addition of small amounts of water to the salt, such as amounts between 0.1 and 20% by weight may substantially reduce the viscosity thereby allowing adaption to the application in question without substantially increasing the necessary amount of the ethoxyquin salt for the particular purpose.

Salts of the above-described kind are also soluble/miscible in lower alkanoic acids. Thus, the invention also relates to a solution of an ethoxyquin salt of an alkanoic acid containing 1-5 carbon atoms in an alkanoic acid containing 1-5 carbon atoms or in a mixture of such alkanoic acids. In such a solution, the ratio by weight between ethoxyquin base and the alkanoic acid or mixture thereof is in the range of 1:1000 to 5:1, in particular 1:100 to 5:1, especially 1:10 to 5:1.

The advantage of the above-described solutions of ethoxyquin salts in lower alkanoic acids is that such acids, e.g. formic acid, propionic acid, and isobutyric acid, are also employed as silaging agents, and the solutions of the ethoxyquin salts in the lower alkanoic acids thereby offer an easily dispersable combination of silaging agent and antioxidant for the production of silage.

It has also been found that inorganic acid addition salts of ethoxyquin are also soluble in lower alkanoic acids to a far greater extent than in water. Thus, the invention also relates to a solution of an inorganic acid addition salt of ethoxyquin in an alkanoic acid containing 1-5 carbon atoms or a mixture of such alkanoic acids. As an example of the increased solubility it may be mentioned that the previously known ethoxyquin hydrochloride only has a solubility of about 5% by weight in water, whereas the solubility in formic acid is about 40% by weight.

Preferred inorganic acid addition salts in the above-described solution are the hydrochloride, sulphates or phosphates, in particular the hydrochloride.

The ratio by weight between the inorganic ethoxyquin salt and the alkanoic acid or mixture thereof may be in the range of 1:1000–5:1, preferably 1:1000–5:1, especially 1:50–5:1.

Salts of ethoxyquin with an alkanoic acid containing 1–5 carbon atoms may be prepared by a method comprising mixing ethoxyquin with the alkanoic acid, the ethoxyquin optionally being dissolved in a solvent such as an aliphatic hydrocarbon, an aromatic hydrocarbon, or a halogenated hydrocarbon. It is preferable that the acid employed is formic acid.

As examples of aliphatic hydrocarbon solvents may be mentioned pentane, hexane, heptane, octane or nonane or mixtures thereof such as mixtures defined by means of boiling point intervals, viz. petroleum ethers with such boiling point intervals as 40°–60° C., 60°–80° C., 80°–100° C. 100°–120° C. or the like. As examples of aromatic hydrocarbons may be mentioned benzene or aliphatic substituted benzene such as toluene or xylene, or other substituted benzenes such as nitrobenzenes. Halogenated hydrocarbons may comprise both halogenated aliphatic hydrocarbons such as methylene chloride, chloroform, carbontetrachloride, trichloroethylene, or perchloroethylene, or halogenated aromatci hydrocarbons such as chlorobenzen, dichlorobenzene or the like.

The mixing of ethoxyquin and the alkanoic acid, whether the ethoxyquin is dissolved in a solvent of the above-described type or not, may be carried out at a temperature within a broad range, such as between 0° C. and 100° C., e.g. at room temperature.

The present invention also concerns the use as an antioxidant or as an anti-fruit scab agent of a salt of ethoxyquin with an alkanoic acid containing 1–5 carbon atoms. The invention further relates to the same uses of a solution of a salt in an alkanoic acid containing 1–5 carbon atoms or in a mixture of such alkanoic acids or of a solution of an inorganic acid addition salt of ethoxyquin in an alkanoic acid containing 1–5 carbon atoms or a mixture of such acids.

In the above described use, the alkanoic acid salt of ethoxyquin, the solution thereof in an alkanoic acid or the solution of an inorganic acid addition salt of ethoxyquin in an alkanoic acid may be utilized in aqueous solutions with concentrations, calculated on ethoxyquin itself, ranging from 0.1 ppm to 10%, in particular 0.5 ppm to 1%, especially 1–100 ppm, such as 1–10 ppm.

Finally, the invention also relates to a citrate of ethoxyquin. Such salts are novel compounds and may be used as a starting material for preparing the other salts of the invention and may also be dissolved in an alkanoic acid containing 1–5 carbon atoms or in a mixture of such alkanoic acids.

Citrates of ethoxyquin may conveniently be prepared by reacting ethoxyquin with citric acid whereby the citric acid may suitably be dissolved in a solvent in which the citric acid and ethoxyquin are soluble, but in which the ethoxyquin citrate formed may only be partially soluble. The reaction may take place at any temperature in a broad range, e.g. 0°–100° C., such as room temperature. If the citrate is partly soluble in the solvent, the resulting salt may be isolated by removal of the solvent. As examples of useful solvents may be mentioned lower alcohols, such as methanol, ethanol propanol, isopropanol or butanol, in particular isopropanol.

The salts of the invention, in particular citrates of ethoxyquin appear to be particularly useful for such applications as the antioxidative protection of for instance fishmeal pressed into pellets. The pressing of pellets tends to allow pure ethoxyquin, whether applied per se or in an aqueous emulsion, or even when applied absorbed into silica gel, to seep out from the individual pellets to the surface thereof and thereby being rendered more or less useless by oxidation from the surrounding air. The salts of the invention, due on the one hand to their ionic nature and on the other hand, in the case of ethoxyquin citrate, to their crystalline nature, appear not to be subject to this seepage, and they will therefore be in a better position to protect the actual material, such as the above-mentioned fishmeal, from oxidation.

In the case of ethoxyquin citrate, there is also a possibility of a synergistic effect, in that citric acid or partly ionized citric acid may function as a coordinating or chelating compound to bind any present amounts of iron or copper ions. Such a binding of iron and copper may further contribute to the oxidation-protective effect of the ethoxyquin citrate, since it is well known that such metals may function as catalysts for the oxidative degradation of e.g. fats, that is the formation of rancidity.

In the literature (Jensen, Preben Moller; Jorgensen, Gunnar (Denmark) Beret. Statens Husdyrbrugsfors, 1975, 427, 79 pp. (Danish)) experiments are described in which herring silage for mink feed was treated with formic acid and ethoxyquin separately. There is no disclosure as to any possibility that this treatment gives rise to the formation of ethoxyquin formiate in the silage, and it is anyway obvious that the problems concerning the use of ethoxyquin itself, i.e. high viscosity and low solubility in water, still persist in this work.

The invention is further illustrated by the following examples which, however, are not construed to be limiting.

EXAMPLE 1

Ethoxyquin formiate

The formiate of ethoxyquin was prepared by mixing equimolar amounts of ethoxyquin (100 g, purity about 99.9%) and formic acid (21.1 g, purity 99–100%) in a flask with stirring at room temperature. The resulting salt was liquid and could not be induced to crystallize even following cooling to −18° C. The salt was soluble in water at pH lower than 3, and in formic, acetic and propionic acid, and also in isopropanol, acetone and ethylacetate. The salt was, unlike ethoxyquin itself, insoluble in petroleum ether, chloroform and carbon tetrachloride.

The pure ethoxyquin formiate, ethoxyquin formiate with 3% by weight of water added and with 15% of water added had viscosities of 600 cps, 300 cps and 80 cps, respectively, at 20° C. determined on a Brookfield LVT viscosimeter. Ethoxyquin formiate with 15% by weight of water added further had a viscosity of 100 cps at 5° C. and 280 cps at about 0° C.

EXAMPLE 2

Ethoxyquin acetate dissolved in acetic acid 100 g of ethoxyquin and 153.4 g of glacial acetic acid were mixed with stirring at room temperature. Hereby was obtained a 50% by weight solution of ethoxyquin acetate in glacial acetic acid. The solution had a viscosity of 60 cps at 20° C.

EXAMPLE 3

Ethoxyquin propionate 100 g of ethoxyquin and 34 g of 100% propionic acid were mixed with stirring at room temperature. The resulting salt was liquid and had a viscosity of 100 cps at 20° C. With 5% of water added the viscosity was reduced to 60 cps at 20° C.

EXAMPLE 4

Ethoxyquin citrate

To a solution of 19.2 g of citric acid in 100 ml isopropanol were dropwise added 21.73 g of ethoxyquin with stirring at room temperature. The isopropanol was removed at low pressure, and the residue was recrystallized from isopropanol giving a white crystalline product with a melting point of 113° C. The ethoxyquin citrate had a solubility in water of approximately 3–4% by weight but was easily soluble in formic acid.

I claim:

1. A method for the antioxidative protection of bulk materials which comprises combining a bulk material with an antioxidative effective amount of a $C_1$–$C_5$ alkanoic acid salt of ethoxyquin.

2. The method according to claim 1 wherein said bulk material is fish meal or grass meal.

3. A salt solution consisting of a $C_1$–$C_5$ alkanoic acid salt of ethoxyquin and a $C_1$–$C_5$ alkanoic acid or a mixture of such acids.

4. The salt solution as claimed in claim 3, wherein said alkanoic acid is formic acid.

5. A salt solution consisting of a $C_1$–$C_5$ alkanoic acid addition salt of ethoxyquin and a $C_1$–$C_5$ alkanoic acid or a mixture of said alkanoic acids wherein the ratio between said $C_1$–$C_5$ alkanoic acid addition salt of ethoxyquin and said $C_1$–$C_5$ alkanoic acid or mixture of said alkanoic acids is in the range of 1:1000 to 5:1.

6. A salt solution consisting of a $C_1$–$C_5$ alkanoic acid addition salt of ethoxyquin and a $C_1$–$C_5$ alkanoic acid or a mixture of said alkanoic acids wherein the ratio between said $C_1$–$C_5$ alkanoic acid addition salt of ethoxyquin and said $C_1$–$C_5$ alkanoic acid or mixture of said alkanoic acids is in the range of 1:100 to 5:1.

7. A salt solution consisting of a $C_1$–$C_5$ alkanoic acid addition salt of ethoxyquin and a $C_1$–$C_5$ alkanoic acid or a mixture of said alkanoic acids wherein the ratio between said $C_1$–$C_5$ alkanoic acid addition salt of ethoxyquin and said $C_1$–$C_5$ alkanoic acid or mixture of said alkanoic acids is in the range of 1:10 to 5:1.

8. The salt solution as claimed in claim 5, wherein said alkanoic acid is formic acid.

9. The salt solution as claimed in claim 6, wherein said alkanoic acid is formic acid.

10. The salt solution as claimed in claim 7, wherein said alkanoic acid is formic acid.

* * * * *